United States Patent [19]

Oksman et al.

[11] Patent Number: 5,302,345
[45] Date of Patent: Apr. 12, 1994

[54] ELECTROCHEMICAL CONTACT LENS DISINFECTION AND NEUTRALIZATION SYSTEM

[76] Inventors: Henry C. Oksman, 140 Morris La., Scarsdale, N.Y. 10583; Joseph Eisner, 219 E. 32nd St., New York, N.Y. 10016

[21] Appl. No.: 117,922

[22] Filed: Nov. 4, 1987

Related U.S. Application Data

[63] Continuation-in-part of Ser. No. 74,703, Jul. 17, 1987, abandoned.

[51] Int. Cl.$^5$ .............................................. A61L 2/18
[52] U.S. Cl. ............................... 422/30; 134/1; 134/27; 204/130; 204/149; 422/22; 422/28; 422/292; 422/297; 422/300
[58] Field of Search ............... 422/28, 30, 292, 297, 422/300, 22; 204/130, 149, 232, 271; 134/1, 27

[56] References Cited

U.S. PATENT DOCUMENTS

| | | | |
|---|---|---|---|
| 2,158,698 | 5/1939 | Hettinger | 422/22 x |
| 3,334,035 | 8/1967 | Dews et al. | |
| 3,912,451 | 10/1975 | Gaglia, Jr. | 422/30 |
| 4,011,941 | 3/1977 | Parsons | 206/5.1 |
| 4,396,583 | 8/1983 | LeBoeuf | 206/5.1 X |
| 4,521,375 | 6/1985 | Houlsby | 422/30 X |
| 4,568,517 | 2/1986 | Kaspar et al. | 422/30 |
| 4,643,876 | 2/1987 | Jacobs et al. | 422/28 x |
| 4,687,997 | 8/1987 | Tao | 422/28 X |
| 4,732,185 | 3/1988 | Cowle et al. | 134/84 |
| 4,836,859 | 6/1989 | Konishi et al. | 422/20 X |
| 4,839,004 | 6/1989 | Castellini | 422/22 X |
| 4,892,706 | 1/1990 | Kralovic et al. | 422/37 x |
| 4,971,773 | 11/1990 | Rohrer et al. | 422/22 X |

FOREIGN PATENT DOCUMENTS

| | | | |
|---|---|---|---|
| 2550946 | 3/1985 | France. | |
| 50-75573 | 6/1975 | Japan | 204/149 |
| 2094992A | 9/1982 | United Kingdom. | |
| 2200653 | 8/1988 | United Kingdom. | |

OTHER PUBLICATIONS

Alexandrov, et al. "Principles of Plasma Electrodynamics," Springer-Verlag, N.Y, N.Y., pp. 3–5.

Primary Examiner—Jill A. Johnston
Attorney, Agent, or Firm—Fiddler Levine & Mandelbaum

[57] ABSTRACT

A method of and apparatus for generating superoxides and other free radicals for cleaning and sterilizing contact lenses tonometers and other poorly oxidizing objects in an electrolytic solution which may optionally include an antiseptic such as hydrogen peroxide enzymes and soaps and for neutralizing the above agents by using electrolysis to decompose the peroxide and to generate free radicals that neutralize the enzymes and soaps and sterilize. The apparatus includes a timer for controlling the process and indicating when sterilization and neutralization are taking place and when they have been completed.

20 Claims, 3 Drawing Sheets

ELECTROCHEMICAL CONTACT LENS DISINFECTION AND NEUTRALIZATION SYSTEM

BACKGROUND OF THE INVENTION

This application is a continuation-in-part of patent application Ser. No. 07/074,703, filed Jun. 17, 1987, now abandoned.

Contact lenses, and porous soft contact lenses in particular, must be periodically disinfected to control growth of bacteria on their surfaces which, if left unchecked, could infect the eyes of the wearer. Ordinarily, the lenses are removed each evening before the wearer retires to sleep and are then reinserted into the eyes upon awakening. This provides an opportunity to disinfect the lenses by their placement in an antiseptic solution, typically one containing chemicals such as hydrogen peroxide although other disinfectants such as sorbic acid may also be used.

The hydrogen peroxide solution is an eye irritant. Hence, any latent trace of the peroxide solution that remains on the lens surface or is absorbed into a porous lens is likely to cause the wearer extreme discomfort, if not pain. It is therefore necessary to remove or neutralize any residual peroxide in the contact lenses. Other chemical disinfectants are also irritating in varying degrees.

Since hydrogen peroxide is relatively unstable and decomposes into water and oxygen, allowing the solution to stand, exposed to atmospheric conditions at ambient temperatures, will eventually result in neutralization of the solution. However, the time necessary for effective neutralization to occur is typically on the order of several days. The prospect of being unable to use contact lenses for several days presents the user with an intolerable situation.

It is known in the prior art to neutralize the disinfectant peroxide solution through the use of chemical additives. See, e.g., U.S. Pat. No. 4,568,517 to Kaspar et al. which discloses a contact lens disinfecting system wherein a chemical neutralizer, e.g. sodium sulfite or sodium thiosulfate is added to the disinfecting solution and U.S. Pat. No. 4,521,375 to Houlsby for Sterilizing Treatment with Hydrogen Peroxide and Neutralization of Residual Amounts Thereof which discloses a contact lens disinfecting system wherein a chemical neutralizer consisting of sodium pyruvate is used. However, these result in the solution, and lenses, being left with other undesirable byproducts of the chemical neutralization.

A more effective solution to the neutralization problem has been found in the use of one or more catalysts to enhance the decomposition of a hydrogen peroxide solution The use of catalytic agents to accelerate the neutralization of a hydrogen peroxide solution absorbed by contact lenses in the course of sterilization is disclosed in U.S. Pat. No. 3,912,451 to Gaglia, Jr. for a Method for Removing Hydrogen Peroxide from Soft Contact Lenses. Although Gaglia's method represents an improvement over some prior methods, specifically the ambient decomposition method, in that it substantially shortens the decomposition time, it still takes at least six (6) hours to reduce the percentage of peroxide to an acceptable level for contact lens wear.

Another method for disinfecting contact lenses, disclosed in U.S. Pat. No. 4,202,740 to Stoner et al., uses electrically charged ions as the disinfectant. In this method the case holding the contact lenses must be made of a conducting material to serve as a bipolar system whereby the ions flowing through the electrolyte decontaminate the contact lens. If there is an uneven current distribution shadows result and the disinfection is incomplete. For proper operation of the latter electrolysis method, the voltages must be kept below the potential at which electrolytic oxygen and chloride from the $H_2O$ and $NaCl$ are generated, otherwise oxidation of the case material, which is conductive, will occur and cause uneven current distribution.

SUMMARY OF THE INVENTION

The instant invention overcomes the aforementioned problems of the prior art in substantially lessening the time for effective cleaning and sterilization of contact lenses and neutralization of the disinfectant solution through the use of electrolysis. The use of hydrogen peroxide and free radical electrolysis for sterilization in a contact lens disinfecting environment according to the instant invention should not be confused with the use of electrolysis with ion current for sterilization of contact lenses per se without a disinfectant solution as disclosed in U.S. Pat. No. 4,202,740 to Stoner et al. for Apparatus and Method for Disinfecting Objects.

Electrolysis can also achieve disinfection by the generation of certain free radicals such as $H_2$ and $O_2$ and pH changes when the electrolyte used in the solution is more stable than the water molecule and when the electrolyte itself generates additional free radicals that are not destructive to the material to be disinfected. Therefore in the electrolytic system of the instant invention the amount of $H_2O_2$ can be reduced below the standard three percent (3%) used in solutions typical of the prior art. If the $H_2O_2$ were completely removed from the electrolytic solution sterilization would still occur but would take a somewhat longer period of time. Without $H_2O_2$ the disinfection rate can be increased with increased current. The generated free radicals and pH changes can, in addition to disinfection, be used to neutralize other agents such as cleaning enzymes and soaps added to the electrolyte.

More specifically, the instant invention provides an apparatus and method for disinfecting contact lenses, tonometers, plastic medical equipment and other poorly oxidizing objects by immersion in a solution with or without hydrogen peroxide, followed by subjecting the solution to electrolysis to rapidly decompose the hydrogen peroxide and at the same time generate free radicals so that together the effectiveness of the disinfection is increased and at the end of the process render the solution neutral so that it is compatible with the natural liquid secretions on the eye, thereby permitting the user to wear the lenses without undue delay.

It is therefore an object of the invention to provide an apparatus and method for disinfecting contact lenses, tonometers, plastic medical equipment and other poorly oxidizing objects effectively, conveniently and rapidly.

Another object of the invention is to provide an apparatus and method for disinfecting contact lenses, tonometers, plastic medical equipment and other poorly oxidizing objects without leaving any undesirable residue of chemical neutralizers or hydrogen peroxide on the lenses.

Still another object of the invention is to provide an apparatus and method for disinfecting contact lenses, tonometers, plastic medical equipment and other poorly oxidizing objects wherein the lenses may be worn soon after they are sterilized without harm or discomfort caused by the disinfecting solution.

An additional object of the invention is to provide an apparatus and method for disinfecting contact lenses, tonometers, plastic medical equipment and other poorly oxidizing objects which allows for a time period prior to electrolysis during which an enzyme or other chemical agent can clean the lenses and sterilization of the lenses and neutralization of the chemicals occurs thereafter.

Another additional object of the invention is to provide an apparatus and method for disinfecting contact lenses, tonometers, plastic medical equipment and other poorly oxidizing objects with a pH sensitive enzyme followed by electrolysis to neutralize the enzyme.

A further object of the invention is to provide an apparatus and method for disinfecting contact lenses, tonometers, plastic medical equipment and other poorly oxidizing objects wherein the user is signaled to indicate when the sterilization and neutralization process is under way and when it is completed.

Still a further object of the invention is to provide an apparatus and method for disinfecting contact lenses, tonometers, plastic medical equipment and other poorly oxidizing objects quickly with or without $H_2O_2$ in a solution that need not be physiologic, i.e., a neutral pH.

An additional further object of the invention is to provide an apparatus and method for generating free radical superoxides not only for disinfection of inanimate objects, but also for use on living tissue, e.g., cataracts.

Other and further objects of the invention will be apparent from the following drawings and description of a preferred embodiment of the invention in which like reference numerals are used to indicate like parts in the various views.

DESCRIPTION OF THE PREFERRED EMBODIMENT

Figure 1:
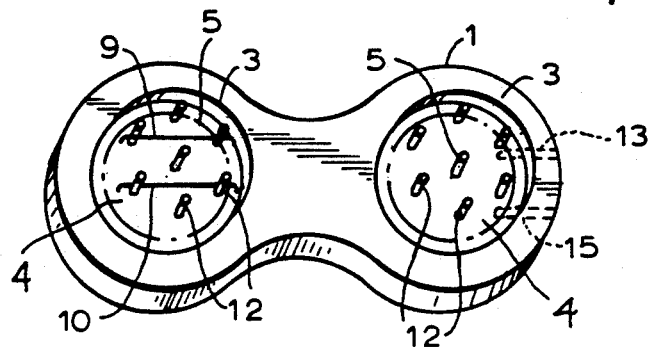
FIG. 1 is a perspective view of part of the apparatus of a preferred embodiment of the invention.
Figure 2A:
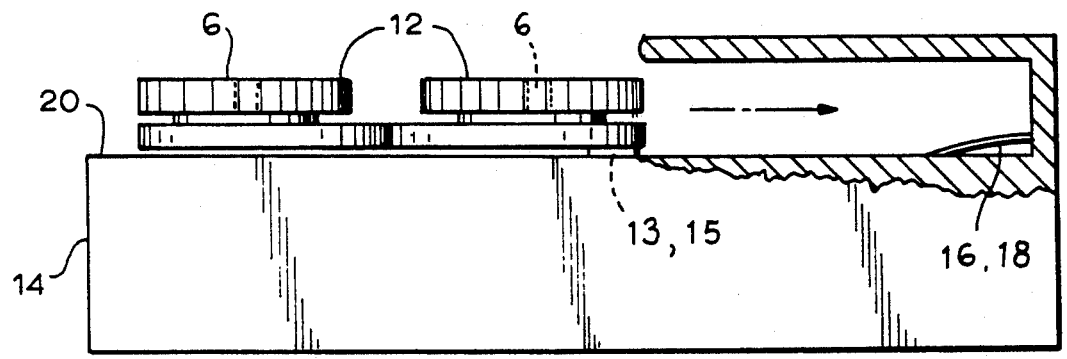
FIG. 2(a) is an elevation view of the apparatus of FIG. 1 installed in an environment including additional apparatus of a preferred embodiment of the invention.
Figure 2B:
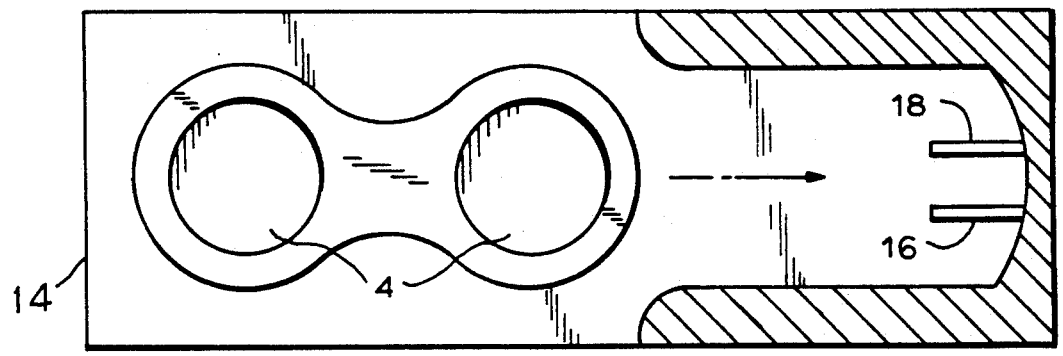
FIG. 2(b) is a plan view of the apparatus of FIG. 2(a).

Referring now to the drawings, there is shown a container in the form of a lens case 1 containing water and/or a disinfectant solution 3 in two chambers 4 in which each one of a pair of contact lenses 5 is immersed. The lens case 1 can be made of nonconductive materials such as glass, most rigid or semi-rigid plastics, or any other material which is not significantly chemically reactive with hydrogen peroxide or free radicals generated in the disinfecting process. The lens case 1 is provided with circular covers 2 which can be threaded onto the the lens case 1 to seal the corresponding circular chambers 4 thereby preventing leakage of the solution 3.

Typically the solution 3 will be water containing from zero to three percent (0%-3%) hydrogen peroxide and a small amount, e.g., 102 milimoles of sodium sulfate, $Na_2SO_4$, or 153 milimoles of calcium sulfate, $Ca_2SO_4$, or potassium bromide (KBr), sodium bromide (NaBr), sodium iodide (NaI), or a similar salt to render the solution conductive in order to enhance the electrolysis process. Phosphate buffers, e.g., $NaH_2PO_4$, $Na_2HPO_4$, or $Na_3PO_4$, may be added to maintain pH constant when necessary. Other phosphated buffers wherein metals from classes IA or IIA of the periodic table of elements are substituted for sodium can be used. Salts such as sodium chloride NaCl and potassium chloride KCl which break down into gaseous components, i.e., chlorine, have been found less desirable for physiologic conditions in that the gaseous byproducts can evaporate leaving hydroxyl ions which can form strong bases such as sodium hydroxide and potassium hydroxide which can chemically damage or destroy contact lenses. When physiologic conditions are not required, small amounts of NaCl can be added to $Na_2SO_4$ to cause generation of chlorine and hydroxides both of which are strong disinfectants. Metals from classes IA and IIA of the periodic table of the elements can be substituted for sodium in the various sodium containing salts herein.

The salt is added in sufficient amounts to buffer the solution to a pH rendering it nearly isotonic with the tears secreted about the eyes. The major salt used should have the property of resistance to disintegration in the electrolytic system while small amounts of other salts such as NaCl and the water and hydrogen peroxide are broken down into free radicals.

Mounted adjacent the bottom of the lens case 1 is a pair of elongated thin wire electrodes including an anode 9 and a cathode 11. Electrically connected to the ends of the anode 9 and cathode 11, respectively, are a positive conductor 13 and a negative conductor 15. The electrodes 9 and 11 are preferably made of a metal alloy or other conducting material which is not readily oxidized, e.g. platinum, rhodium, iridium, carbon, platinum rhodium alloy or platinum iridium alloy. For electrode stability an alloy is the preferred choice as pure elements tend to have weaker bonds and degrade more rapidly under high current densities.

While some of the suitable materials may also have a catalytic effect on neutralizing the peroxide solution when used in sufficient quantity as taught by Gaglia, the size of the electrodes, typically about 0.5 mm diameter by 20 mm length is such as to make the amount of electrode material much less than the catalytic amount needed for any material increase in the decomposition of the peroxide by catalytic action. Absent the electrolysis process taught herein, the insertion of the electrodes in the sterilizing solution would provide no material advantage over merely allowing the peroxide to normally decompose under ambient conditions.

Also mounted on the bottom of the lens case 1 is an integral array of spacers 12, projecting upwardly from the bottom interior surface of the lens case 1, on which the lenses are supported to permit the solution 3 to flow between the bottom surface and lenses so that the lenses are surrounded on all sides by the disinfectant solution 3. The lens case covers 2 are provided with openings 6 to permit oxygen to escape. Optionally, an oxygen permeable liquid tight seal may be disposed within the openings in the covers 2 to further ensure against leakage of the disinfectant solution as will be known to those skilled in the art. Where no hydrogen peroxide is used and the disinfection period is kept short, the need for the openings 6 may be obviated.

Figure 3:
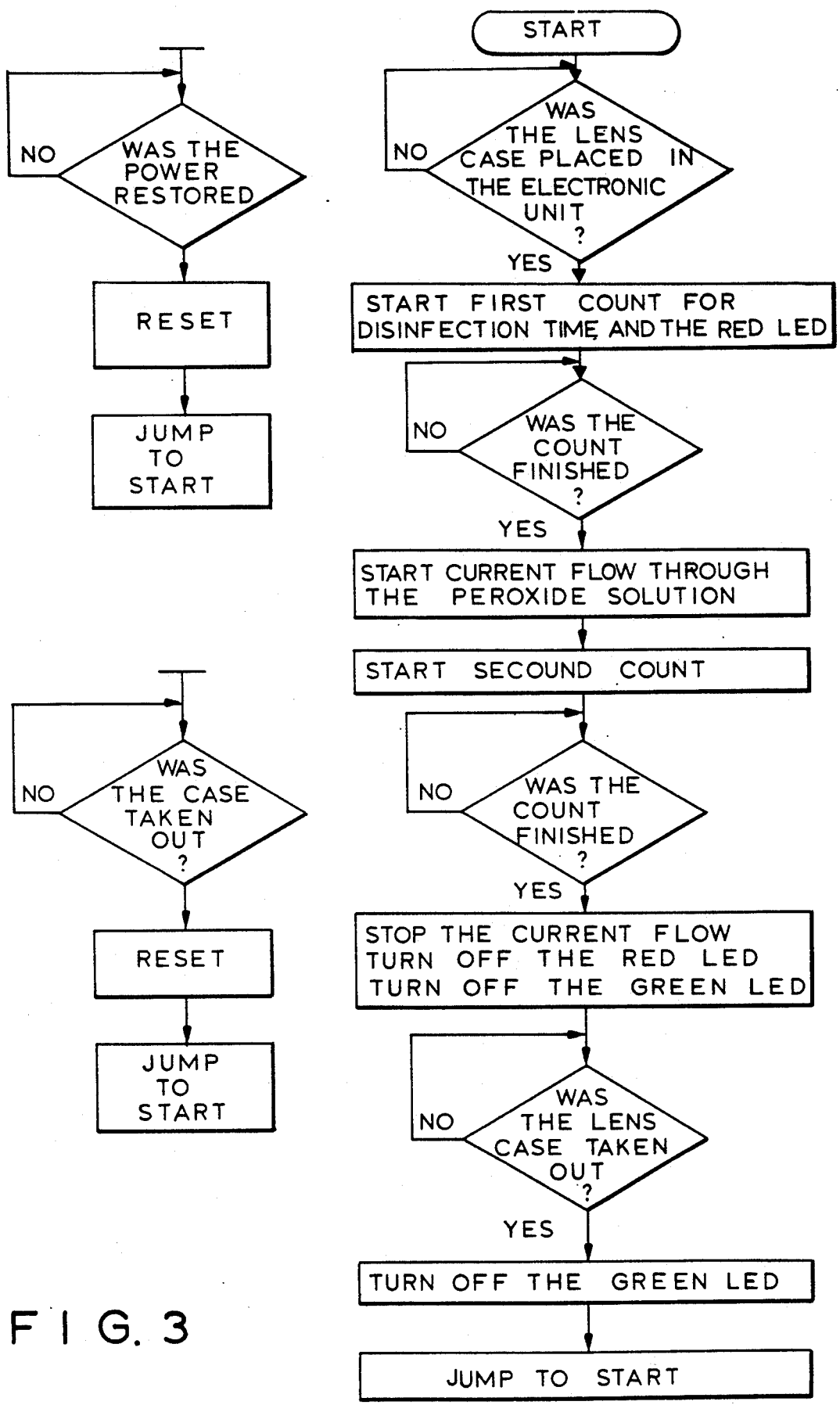
FIG. 3 is a flow diagram for the method of a preferred embodiment of the invention.
Figure 4:
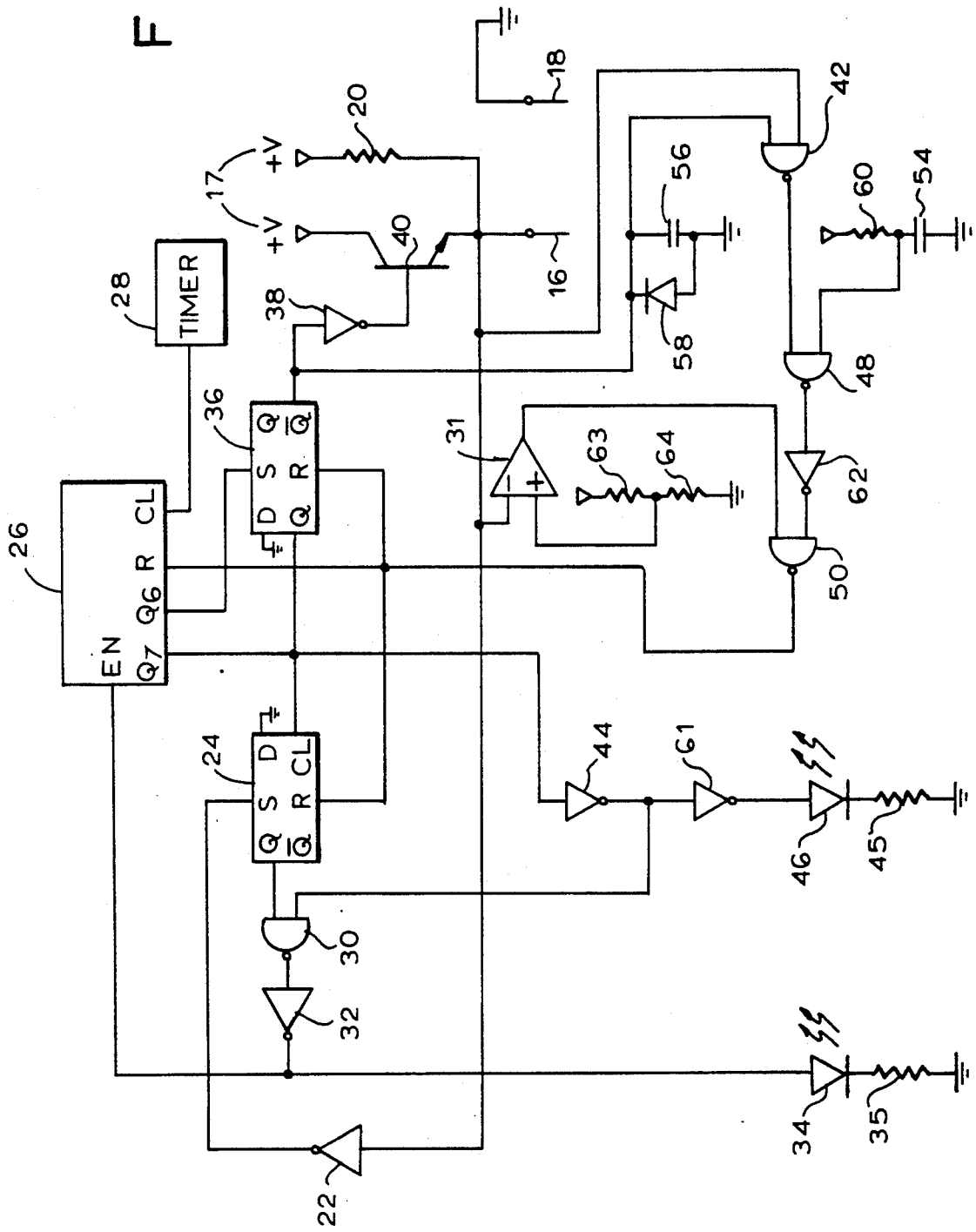
FIG. 4 is a schematic circuit diagram of part of the apparatus of a preferred embodiment of the invention.

A source 17 of electrical potential which serves as a power supply provides the energy for rapid decomposition of the sterilization solution 3. The source 17 may be A.C. or D.C. In the preferred embodiment of the invention the source 17 is a conventional storage battery with a D.C. potential of between 1.5 and 20 volts, high enough to generate free radicals. A power source 17 capable of generating square waves having peaks of sufficient amplitude to generate free radicals is alternatively preferred. A timing and control unit 14 is provided for carrying out the lens cleaning, sterilization and disinfectant neutralization processes of the invention in accordance with the flow diagram of FIG. 3. The construction and operation of the timing and control unit is described with reference to FIG. 4.

The timing and control unit 14 governs three process time periods. During the first period, the lenses are placed in a salt solution as previously described which may contain cleaning agents, e.g. including one or more enzyme ingredients and/or soaps, and or an antiseptic, e.g., hydrogen peroxide. During the first time period, the cleaning agents, soaps or enzymes, if present, remove contaminants from the lenses and the antiseptic, if present, kills infectious microorganisms.

During the second time period, electric current is applied to the solution. The current is at a level in the rang of 5 to 300 milliamperes, sufficient to cause the generation of free radicals of hydrogen and oxygen as well as pH change from $Na_2SO_4$ electrolysis, all of which have an antiseptic effect and sanitize the lenses, even in the absence of an antiseptic additive. The electrolysis, disinfects by pH changes as well as free radical formation and also neutralizes any residual hydrogen peroxide, and any enzymes or soaps added, thereby leaving a weak salt solution having a tonicity near the tonicity of the natural fluids surrounding the eyes. The first few seconds following the current interruption are included in the second period. It is during this time that the free radicals dissipate and the pH returns to the physiologic range.

The third time period follows the interruption of the electrolysis current following the disinfection of the lenses and neutralization of the solution 3. It is during the third time period that the cleaned, sterilized and neutralized lenses may be removed from the timing and control unit 14.

A pair of electrodes 16 and 18 project upwardly from a planar mounting surface 20 on the timing and control unit 14 for contacting the conductors 13 and 15 respectively on the lens case 1. Electrode 18 is grounded while electrode 16 is normally maintained at the positive battery voltage to which it is connected through a resistor 20 which in the preferred embodiment of the invention has a resistance of approximately 1 megohm. When the electrodes 16 and 18 make contact with the conductors 13 and 15 which are bridged by the ionized solution 3, a current path is completed between the electrodes 16 and 18.

Upon completion of the current path between the electrodes 16 and 18, the input to an inverter 22 is brought to ground potential. The low signal input to inverter 22 results in a high signal at the output of the inverter 22 which sets a flip-flop 24. The flip-flop 24 is a type 4013 CMOS. The resultant high signal at the Q output of flip-flop 24 feeds NAND gate 30. The other input of NAND gate 30 is connected to the output of an inverter 44. When both inputs of NAND gate 30 are high, i.e., the lens case 1 is in the timing and control unit 14 and the cleaning process has not yet been completed, the output of NAND gate 30 is low. This signal is applied to an inverter buffer 32 and enables an eight bit counter 26, which can be a type 4520 CMOS integrated circuit, to be ̇ı counting pulses applied by a type 555 integrated c: ;uit timer 28 which in the preferred embodiment of the invention generates one pulse approximately every ten seconds. Inverter 44 indicates the status of the eighth bit $Q_7$ of the counter 26, i.e., whether the cleaning process is completed as will be later explained.

The inverter buffer 32, which can be a 4049 CMOS integrated circuit, is connected to the anode of a red light emitting diode (L.E.D.) 34 having a cathode connected to ground through a resistor 35. This causes the L.E.D. 34 to light while the cleaning and, where an antiseptic such as hydrogen peroxide is used, partial disinfection of the lenses takes place.

After a predetermined time, dictated by the frequency of the high marking the completion of the cleaning portion of the process. The high output at the seventh bit of counter 26 sets a flip-flop 36 which can also be a type 4013 CMOS. This causes the $\overline{Q}$ output of flip-flop 36 to go low, and the output of an inverter buffer 38 which is connected to the base of transistor 40 to go high, thereby turning on transistor 40 to begin the generation of the free radicals as well as neutralizing the hydrogen peroxide ($H_2O_2$) and/or any added soaps or enzymes.

When transistor 40 is turned on, battery current flows through the ionized salt-containing sterilization solution 3 while the counter 26 continues to count the pulses from timer 28. It has been found that the electrolysis current should preferably be in the range of 2–120 milliamperes per cubic centimeter of solution. In the preferred embodiment of the invention, wherein each of the chambers 4 is filled with approximately 2.5 c.c. of solution, the total electrolysis current to generate the radicals in the solution 3 in both chambers 4 is approximately 10–600 milliamperes. The current flow also causes the peroxide, if any is present, to be reduced to water and free oxygen in accordance with the following relationship.

$$H_2O_2 \rightarrow H_2O + O_2$$

Also, free hydrogen and oxygen radicals are generated in accordance with $$H_2O_2 \rightarrow H_2 + O_2 \text{ and } H_2O \rightarrow H_2 + O_2$$

Also, basic and acidic ions are generated in accordance with:

$$Na_2SO_4 \rightarrow 2(Na+OH\text{-}) + H + _2SO_4-$$

$$2NaCl \rightarrow 2Na + OH\text{-} \\ + 2H + Cl \rightarrow 2Na + OH\text{-} + H_2 + Cl_2$$

This electrolysis procedure by which the solution 3 creates the free radicals and also neutralizes the disinfectant solution continues for a predetermined time until the eighth bit $Q_7$ of the counter 26 goes high. The output of the eighth bit of the counter 26 is connected to the clock inputs of the flip-flops 24 and 36. Hence, when the output of the eighth bit of the counter 26 goes high, i.e., after the disinfection with the free radicals that were generated by electrolysis of the solution 3 has been completed, the low state at the grounded D input to each of the flip-flops 24 and 36 is loaded into the respective Q outputs. The low signal at the Q output of flip-flop 24 turns off the red L.E.D. 34 and disables the counter 26. The high signal at the 0 output of flip-flop 36 turns off transistor 40 thereby halting the electrolysis current flow.

The output of the eighth bit of the counter 26 is connected to the inverter buffer 44, which can be a 4049 CMOS integrated circuit. Inverter buffer 44 is connected to inverter buffer 61 which is, in turn, connected to the anode of a green light emitting diode (L.E.D.) 46 having a cathode connected to ground through a resistor 45. This causes the green L.E.D. 46 to light after the sterilization by radicals with or without peroxide and the neutralization by electrolysis of the solution 3 has been completed, thereby signaling the user to remove the lens case 1 from the timing and control unit 14. The cleaned, sterilized and neutralized lenses can then be removed from the lens case 1 and safely inserted into the eyes. Removal of the lens case 1 causes the flip-flops 24 and 36 to be reset at which time the counter 26 is initialized and the L.E.D.s 34 and 46 are turned off.

The timing and control unit 14 is automatically initialized either when the lens case 1 is removed from the timing and control unit 14 or system battery power is removed and then reapplied. The reset logic for initializing the system is provided by NAND gates 48 and 50.

A NAND gate 42 has its respective inputs connected to the output Q of flip-flop 36 and to the electrode 16 for generating a low output signal when the transistor 40 is off and the case 1 is out of the timing and control unit 14. Capacitor 56 and diode 58 prevent sudden changes in the voltage at the input of NAND gate 42 which could upset the sequence for reinitializing the system.

The low signal from NAND gate 42 is then applied to NAND gate 48. NAND gate 48 has its other input connected to capacitor 54 and resistor 60. When power is reapplied after being off, the capacitor 54 is charged through resistor 60 and provides a low signal pulse. The low signal pulse is applied to the other input of NAND gate 48. This low signal pulse causes a reset signal to be generated whenever power is restored after being interrupted.

The output of NAND gate 48 is inverted by inverter 62. Operational amplifier 31 has its respective inputs connected to the electrode 16 and to a voltage divider formed by resistors 63 and 64. The values of the resistors 63 and 64 are such that the voltage at the node between them is lower than the voltage at electrode 16 when transistor 40 is on and the case 1 is out of the timing and control unit 14 and higher than the voltage at electrode 16 during any other condition, i.e., the operational amplifier 31 yields a low logic output when transistor 40 is on and the case 1 is taken out of the timing and control unit 14.

NAND gate 50 has its respective inputs connected to the output of inverter 62 and to the output of operational amplifier 31. A high signal output from NAND gate 50 is used to reset counter 26 and flip-flops 24 and 36 when the case 1 is removed from the timing and control unit 14 while transistor 40 is off, or the case 1 is removed from the timing and control unit 14 while transistor 40 is on, or power is restored after being interrupted.

The reset signal from the output of NAND gate 50 is applied to the reset inputs of flip-flops 24 and 36 and turns off the red L.E.D. 34 and 46 if either was previously lit.

In use, the container 1 is partially filled with a sterilizing solution of water ($H_2O$), hydrogen peroxide ($H_2O_2$) and salt ($Na_2SO_4$, $CaSO_4$, NaBr, KBr, NaI, KI, phosphate buffer or other organic salts that ionize but are otherwise stable at the applied potential) in the above stated relative quantities. When the contact lens wearer retires to bed, or at any other time when it is desired to clean and sterilize the lenses, they are inserted into the solution 3 in the lens case 1 which is inserted into the timing and control unit 14 and left there a sufficient time for cleaning, sterilization and neutralization to be achieved, as indicated by the lit red and green L.E.D.s.

The resultant solution is a dilute saline having a tonicity and pH like that of the tears. Hence, to the extent that the solution is absorbed into or remains on the surface of the contact lenses after their removal from the lens case or container 1, it causes no discomfort to the wearer after insertion into the eyes.

Ultrasonic cleaners may be used in conjunction with the apparatus of the invention.

It is to be appreciated that the foregoing is a description of a preferred embodiment of the invention to which variations and modifications may be made without departing from the spirit and scope of the invention. Moreover, the invention is not limited to sterilizing contact lenses and may apply to the disinfection of any article or object which can be cleaned and sterilized by electrolysis. Additionally, the apparatus and method can be used for the treatment of diseased tissue. The application of free radical containing solution is believed to be able to destroy or, at least, retard the growth of infectious viruses and bacteria in living tissue. The apparatus herein described can be used for tissue treatment. It can also be used in the experimental evaluation of the destructive effects of superoxides on the heart muscle and cataracts. In vitro studies can be done using the apparatus to generate free radicals, such as superoxides, in solutions, inserting the tissue into the solution, and observing the effects of the free radicals, e.g., superoxides, on the tissue.

We claim:

1. A method of neutralizing a disinfectant liquid, wherein said liquid contains hydrogen peroxide and a salt, comprising
    immersing first and second electrodes in said disinfectant liquid in spaced relationship, and
    causing an electric current to flow between said electrodes through said liquid.

2. A method of neutralizing a disinfectant liquid according to claim 1 wherein said salt is stable under electrolysis.

3. A method of neutralizing a disinfectant liquid according to claim 2 wherein said salt is selected from the group consisting of sodium sulfate, phosphate buffer, potassium bromide, sodium bromide, potassium iodide and sodium iodide.

4. A method of neutralizing a disinfectant liquid according to claim 1 wherein said current is maintained in the range of 2 to 120 milliamperes per cubic centimeter of solution.

5. A method of sterilizing a contaminated article comprising
    immersing said article in a disinfectant liquid for a time sufficient to allow disinfection thereof, and
    causing an electric current to flow through said liquid between at least two electrodes in contact therewith for a time sufficient to neutralize said disinfectant liquid.

6. A method of sterilizing a contaminated article according to claim 5 further comprising dissolving a salt in said liquid to control the pH thereof and enhance the current flow.

7. Apparatus for performing a process for sterilizing a contaminated article comprising
container means for storing said article,
a disinfectant liquid stored in said container means for at least partially covering said article,
first and second electrode means at least partially in contact within said liquid, said container means including supporting means for maintaining said article disengaged from each of said first and second electrode means,
a current source,
first and second conductor means operatively connected between said respective first and second electrode means and said current source,
means for producing a first signal indicative of the commencement of the process for sterilization of the contaminated article by the disinfectant liquid, and for producing a second signal a predetermined time after said first signal is produced, and
current enabling means responsive to said second signal, enabling current to flow from said current source between said first and second electrode means.

8. Apparatus for sterilizing a contaminated article in accordance with claim 7 wherein said container means comprises spacer means for supporting said article in spaced relationship to a surface thereof to permit said liquid to flow between said article and said surface.

9. Apparatus for sterilizing a contaminated article in accordance with claim 8 wherein said liquid comprises hydrogen peroxide.

10. Apparatus for sterilizing a contaminated article in accordance with claim 9 wherein said liquid comprises an ionized salt.

11. Apparatus for sterilizing a contaminated article in accordance with claim 9 wherein said liquid comprises free radicals of one or more elements contained in the ingredients of said liquid.

12. Apparatus for sterilizing an object in a cleaning and/or disinfectant liquid and thereafter neutralizing the liquid comprising
container means for holding said object in said disinfectant liquid, said container means having a cathode and an anode in contact with said liquid,
and timing said control means releasably connectable to said container means and including first conductor means releasably connectable to said anode, second conductor means releasably connectable to said cathode, power supply means, timer means, and switch means operatively connected to said power supply means, said timer means and at least one of said first and second conductor means for connecting said power supply means to said one of said first and second conductor means at a first predetermined time after said container means is connected to said timing and control means and for disconnecting said power supply means from said one of said first and second conductor means at a second predetermined time after said first predetermined time.

13. Apparatus for sterilizing an object in a cleaning and/or disinfectant liquid and thereafter neutralizing the liquid according to claim 12 further comprising first signal means operatively connected to said timer means and active for a time duration between connection of said container means to said timing and control means and said second predetermined time.

14. Apparatus for sterilizing an object in a cleaning and/or disinfectant liquid and thereafter neutralizing the liquid according to claim 13 further comprising second signal means operatively connected to said timer means and active after said second predetermined time.

15. Apparatus for sterilizing an object in a cleaning and/or disinfectant liquid and thereafter neutralizing the liquid according to claim 12 further comprising sensing means operatively connected to said first conductor means for generating a signal indicative of whether said container means is connected to said timing and control mans, and initializing means operatively connected to said sensing means for resetting said timer means when said container means is not connected to said timing and control means.

16. A method of sterilizing an article comprising
immersing the article in a liquid,
immersing first and second electrodes in said liquid in spaced relationship, and
causing to flow between said electrodes through said liquid an electric current of sufficient magnitude to generate free radicals for disinfecting said article.

17. A method of sterilizing an article according to claim 16 wherein said article and said liquid are disposed in container means formed from a nonconductive material.

18. A method of sterilizing an article according to claim 17 further comprising subjecting said article to a cleaning agent and causing said current to flow at a first predetermined time after said article is subjected to said cleaning agent to generate free radicals for sterilizing said article and/or for neutralizing said disinfecting liquid.

19. A method of sterilizing an article according to claim 18 further comprising interrupting said current at a second predetermined time after said first predetermined time.

20. A method of sterilizing a contaminated article comprising
immersing said article in a liquid salt solution,
causing an electric current to flow through said solution between at least two electrodes in contact therewith for a time sufficient to change the pH thereof whereby said solution is rendered disinfecting,
adding a soap or enzyme to said solution, and
continuing to apply said electric current until the pH of said solution is rendered substantially neutral.

* * * * *